(12) United States Patent
Jeon et al.

(10) Patent No.: US 6,921,366 B2
(45) Date of Patent: Jul. 26, 2005

(54) APPARATUS AND METHOD FOR NON-INVASIVELY MEASURING BIO-FLUID CONCENTRATIONS USING PHOTOACOUSTIC SPECTROSCOPY

(75) Inventors: Kye-jin Jeon, Suwon (KR); Gil-won Yoon, Seoul (KR); In-duk Hwang, Suwon (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 31 days.

(21) Appl. No.: 10/390,614

(22) Filed: Mar. 19, 2003

(65) Prior Publication Data

US 2003/0225320 A1 Dec. 4, 2003

(30) Foreign Application Priority Data

Mar. 20, 2002 (KR) ........................................ 2002-15147

(51) Int. Cl.[7] ................................................ A61B 5/00
(52) U.S. Cl. .................... 600/309; 600/316; 600/322
(58) Field of Search ................................. 600/309–310, 600/476, 473, 443, 446, 437, 407, 438–449, 316

(56) References Cited

U.S. PATENT DOCUMENTS

| | | | |
|---|---|---|---|
| 4,385,634 A | | 5/1983 | Bowen |
| 5,977,538 A | * | 11/1999 | Unger et al. ................. 600/310 |
| 6,070,093 A | * | 5/2000 | Oosta et al. ................. 600/316 |
| 6,212,421 B1 | * | 4/2001 | Vo-Dinh et al. ............. 600/407 |
| 6,264,610 B1 | * | 7/2001 | Zhu ............................ 600/443 |
| 6,390,978 B1 | * | 5/2002 | Irion et al. .................. 600/437 |
| 6,403,944 B1 | | 6/2002 | MacKenzie et al. |
| 6,690,958 B1 | * | 2/2004 | Walker et al. ............... 600/323 |

FOREIGN PATENT DOCUMENTS

| | | |
|---|---|---|
| EP | 0 282 234 | 9/1988 |
| EP | 0 919 180 | 6/1999 |
| EP | 1 048 265 A1 | 11/2000 |
| JP | 11-235331 | 8/1999 |
| WO | 98/38904 | 7/1998 |
| WO | WO 02/15776 A1 | 2/2002 |

OTHER PUBLICATIONS

Ashton, H.S., et al., "Blood Glucose Measurements by Photoacoustics", Photoacoustic and Photothermal Phenomena: 10th Intnl. Conference, Edited by F. Scudieri & M. Bertolotti, pp. 570572, (1999).

Christison, G.B., et al., "Laser Photoacoustic Determination of Physiological Glucose Concentrations in Human Whole Blood", Medical & Biological Engineering & Computing, pp. 284–290, (May 1993).

Heise, H.M., "Technology for Non–Invasive Monitoring of Glucose", 18th Annual International Conference of The IEEE Engineering in Medicine & Biology Society, Amsterdam, 2159–2161 (1996).

* cited by examiner

*Primary Examiner*—Eric F. Winakur
*Assistant Examiner*—Matthew Kremer
(74) *Attorney, Agent, or Firm*—Lee, Sterba & Morse, P.C.

(57) ABSTRACT

An apparatus and method for non-invasively measuring bio-fluid concentrations using photoacoustic spectroscopy includes a light source for irradiating an incident light having a predetermined wavelength band to be absorbed into a targeted component of a living body, an acoustic signal generator for generating a first acoustic signal having a similar frequency band as a photoacoustic signal that is generated when the incident light is absorbed into the targeted component, a ultrasonic translator for detecting the photoacoustic signal and a second acoustic signal that is a modulated signal of the first acoustic signal, a controller for generating the first acoustic signal in a predetermined frequency band, a light detector for detecting an intensity of the incident light, and a calculator capable of calculating a signal compensation value based on the incident light, the photoacoustic signal, and the coefficient of sound wave transmission, and capable of computing a concentration of the targeted component.

37 Claims, 9 Drawing Sheets

APPARATUS AND METHOD FOR NON-INVASIVELY MEASURING BIO-FLUID CONCENTRATIONS USING PHOTOACOUSTIC SPECTROSCOPY

BACKGROUND OF THE INVENTION

1. Field of the Invention

The present invention relates to an apparatus and a method for non-invasively measuring bio-fluid concentrations. More particularly, the present invention relates to an apparatus and a method for non-invasively measuring bio-fluid concentrations using photoacoustic spectroscopy.

2. Description of the Related Art

Even though research has long been carried out worldwide on a method of measuring glucose levels by means of light without actually collecting blood, such research has failed to provide any distinctive results.

Various measurement techniques, such as near infrared absorption, far infrared absorption, Ramann spectroscopy, polarization rotation, Stimulate Ramann, dispersion measurement, temperature measurement, statistical analysis, and pretreatment research, have been adopted in vivo measure bio-fluid concentrations. However, since each of these conventional measurement techniques has several disadvantages, the in vivo measurement of bio-fluid concentrations has not been satisfactorily accomplished.

For example, near infrared absorption has the following disadvantages. First, an absorption peak may not exist at a predetermined frequency. Second, the absorption bands of components may overlap one another. Third, it is difficult to anticipate the concentration of a substance having a low concentration because dispersion easily occurs due to biological tissues. In the case of far infrared absorption, far infrared rays are barely able to penetrate the human body, even though they cause dispersion less frequently, and there exists a distinct absorption peak. In the case of Ramann spectroscopy or polarization rotation, dispersion occurs frequently due to the existence of many dispersion factors in the human body, and thus it is difficult to precisely measure bio-fluid concentrations.

Recently, intensive research has been carried out on an apparatus and method for bio-fluid concentrations measurement by means of photoacoustic spectroscopy. When light enters a test sample, molecules are excited and collide with one another, thereby generating heat. The change of heat causes the change of pressure in an airtight container, which generates an acoustic signal, i.e., a sound wave. The sound wave can then be detected using a microphone.

FIGS. 1 and 2 are diagrams showing a non-invasive photoacoustic measurement device according to the prior art. Referring to FIG. 1, a conventional non-invasive photoacoustic measurement device 10 includes an excitation source 12, a controller/modulator 14, a probe 16, a lock-in amplifier 18, and a processor 20.

In operation, the excitation source 12 generates a sound wave when the excitation source 12 is irradiated onto a biological tissue, such as skin. The sound wave is transmitted to the human body through a transmitter 22, such as a bundle of optic fibers.

The probe 16, as shown in greater detail in FIG. 2, includes a measurement cell 26, a reference cell 28, a window 30, and a differential microphone 32. The sound wave, generated when the excitation source 12 is irradiated onto a tissue 24, passes through the window 30 of the measurement cell 26 and heats air 38 in contact with the tissue 24 in the measurement cell 26 on a regular basis with the same modulated frequency as that of the sound wave. The sound wave is absorbed into a targeted component of the tissue 24, and the air in the measurement cell 26 repeatedly contracts and expands due to the periodic variation of the temperature. As a result, a periodic sound wave having the same modulated frequency as that of the sound wave is generated.

The periodic sound wave inside the measurement cell 26 is detected by the differential microphone 32, a first end 40 of the differential microphone 32 is located in the measurement cell 26 and a second end 42 of the differential microphone 32 is located in the reference cell 28. The measurement cell 26 is located on a first predetermined surface 46 of the tissue 24, onto which laser beams are irradiated. The reference cell 28 is located on a second predetermined surface 48 of the tissue 35, onto which no laser beams are irradiated.

The signals detected by the probe 16 become the outputs of the differential microphone 32 and are transmitted to the lock-in amplifier 18. Among the outputs, the lock-in amplifier 18 extracts only signals of the same frequency as the modulated frequency of the light beams that are generated and irradiated from the excitation source 12 under the control of the controller/modulator 14. The processor 20 analyzes the frequencies of the signals extracted by the lock-in amplifier 18 and derives a polarized acoustic spectrum. The conventional acoustic measurement device determines the concentration of a targeted component based on this polarized acoustic spectrum.

Even though the reference cell 28 attempts to compensate for noise generated by the human body, such as muscular movements, the conventional photoacoustic measurement device illustrated in FIGS. 1 and 2 is not able to precisely represent the state of the human body because the device senses only modulated signals and the signals themselves have predetermined frequency bands.

The aforementioned conventional bio-fluid measurement device using photoacoustic spectroscopy detects infrared laser beams among all laser beams irradiated on a predetermined material from a semiconductor laser, using a photoacoustic detector. Next, the bio-fluid measurement device analyzes bio-fluid concentrations based on acoustic signals detected by the photoacoustic detector. However, due to the fact that the characteristics of transmission of sound waves may vary depending on the person being measured and the body part of the person being measured, this conventional bio-fluid measurement device is not able to measure precisely bio-fluid concentrations, which is similarly a problem with other conventional measurement devices using photoacoustic spectroscopy.

SUMMARY OF THE INVENTION

The present invention provides an apparatus and a method for non-invasively measuring bio-fluid concentrations, the results of which are only minimally affected by differences among people being tested or among parts of the human body being tested.

According to an aspect of the present invention, there is provided an apparatus for non-invasively measuring bio-fluid concentrations. The apparatus includes a light source for irradiating an incident light having a predetermined wavelength band which can be absorbed into a targeted component of a living body on a predetermined part of the living body, an acoustic signal generator for generating a first acoustic signal A1 having a similar frequency band to the frequency band of a photoacoustic signal PA that is generated when the incident light is absorbed into the targeted component of the living body in the vicinity of the predetermined part of the living body, a ultrasonic translator for detecting the photoacoustic signal PA and a second acoustic signal A2 that is a modulated signal of the first acoustic signal A1 due to the acoustic characteristics of the living body, a controller for generating the first acoustic signal A1 in a predetermined frequency band, a light detector for detecting an intensity E of the incident light, and a calculator capable of calculating a signal compensation value N based on an intensity E of the incident light from the light source, and the photoacoustic signal PA input from the ultrasonic translator and a coefficient of sound wave transmission Ac, and capable of computing a concentration C of the targeted component.

Preferably, the apparatus further includes an indicator for indicating the concentration C of the targeted component.

Preferably, the signal compensation value N satisfies the following equation, equation 1:

$$N = \frac{PA}{Es\sqrt{v}\,A_C}, \quad (1)$$

wherein $A_C$ is a coefficient of sound wave transmission, i.e., $$\frac{A2}{A1}.$$

Preferably, the concentration C of the targeted component is proportional to the signal compensation value N.

Preferably, the light detector, the controller, and the calculator are integrated into one unit, or the light detector, the controller, the calculator, and the indicator are integrated into one unit.

Preferably, the acoustic signal generator and the ultrasonic translator are integrated into one unit, or the light source, the acoustic signal generator, and the ultrasonic translator are integrated into one unit.

Preferably, the acoustic signal generator is able to be fixed to a human body using an air pumping method.

Preferably, the light source is any one of a laser diode (LD), a light emitting diode (LED), a laser, a black body radiator, or a lamp.

According to another aspect of the present invention, there is provided an apparatus for non-invasively measuring bio-fluid concentrations. The apparatus includes a light source for irradiating an incident light having a predetermined wavelength band which can be absorbed into a targeted component of a living body on a predetermined part of the living body, a light detector for detecting an intensity E of the incident light and a photoacoustic signal generated when the incident light is absorbed into the targeted component of the living body, an acoustic signal generation/measurement device for detecting a photoacoustic signal PA generated when the incident light is absorbed into the targeted component of the living body, for generating a first acoustic signal A1 having a similar frequency band to the frequency band of the photoacoustic signal PA in the vicinity of the predetermined part of the living body and for measuring a second acoustic signal A2 that is a modulated signal of the first acoustic signal A1 due to the acoustic characteristics of the living body, a controller for controlling the acoustic signal generation/measurement device so that the first acoustic signal A1 in a predetermined frequency band can be generated, and a calculator capable of calculating a signal compensation value N based on the intensity E of the incident light from the light source, and the photoacoustic signal PA input form the ultrasonic translator and a coefficient of sound wave transmission $A_C$, and capable of computing the concentration C of the targeted component.

Preferably, the apparatus further includes an indicator for indicating the concentration C of the targeted component.

Preferably, the signal compensation value N satisfies equation 1 above.

Preferably, the concentration C of the targeted component is proportional to the signal compensation value N.

Preferably, the controller and the calculator are integrated into one unit, or the controller, the calculator, and the indicator are integrated into one unit.

Preferably, the acoustic signal generation/measurement device and the light detector are integrated into one unit, or the light source, the acoustic signal generation/measurement device and the light detector are integrated into one unit.

Preferably, the acoustic signal generator is able to be fixed to a human body using an air pumping method.

Preferably, the light source is any one of a laser diode (LD), a light emitting diode (LED), a laser, a black body radiator, or a lamp.

According to yet another aspect of the present invention, there is provided a method for non-invasively measuring bio-fluid concentrations. The method includes applying an incident light having a predetermined wavelength band which can be absorbed into a targeted component of a living body to a predetermined part of the living body, detecting the intensity E of the incident light and a photoacoustic signal PA generated when predetermined wavelengths of the incident light are absorbed into the targeted component of the living body, generating a first acoustic signal A1 having a similar frequency band to the frequency band of the photoacoustic signal PA in the vicinity of the predetermined part of the living body, detecting a second acoustic signal A2 that is a modulated signal of the first acoustic signal A1 due to the acoustic characteristics of the living body, and calculating a signal compensation value N based on the intensity of the incident light, the photoacoustic signal PA and a coefficient of sound wave transmission $A_C$, and computing a concentration C of the targeted component of the living body.

Preferably, the signal compensation value N satisfies equation 1.

Preferably, the concentration C of the targeted component of the living body is proportional to the signal compensation value N.

According to the present invention, it is possible to compensate for a deviation in the speeds of photoacoustic signals, which are affected by differences among parts of a human body being tested and among people being tested, by correcting the photoacoustic signal using a reference photoacoustic signal. Further, it is possible to measure precisely bio-fluid concentrations by correcting a variation in the transmission characteristics of photoacoustic signals, such as reflection or dispersion, which is caused by the structure of a living body.

BRIEF DESCRIPTION OF THE DRAWINGS

The above and other aspects and advantages of the present invention will become more apparent to those of ordinary skill in the art by describing in detail preferred embodiments thereof with reference to the attached drawings in which.

DETAILED DESCRIPTION OF THE INVENTION

Figure 1:
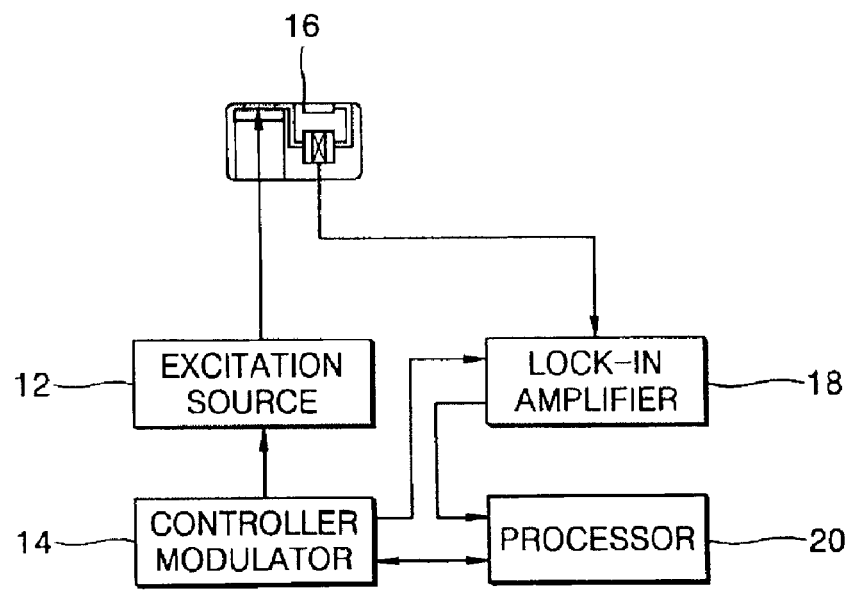
FIG. 1 is a block diagram of a device for non-invasively measuring blood glucose using photoacoustic spectroscopy according to the prior art.
Figure 2:
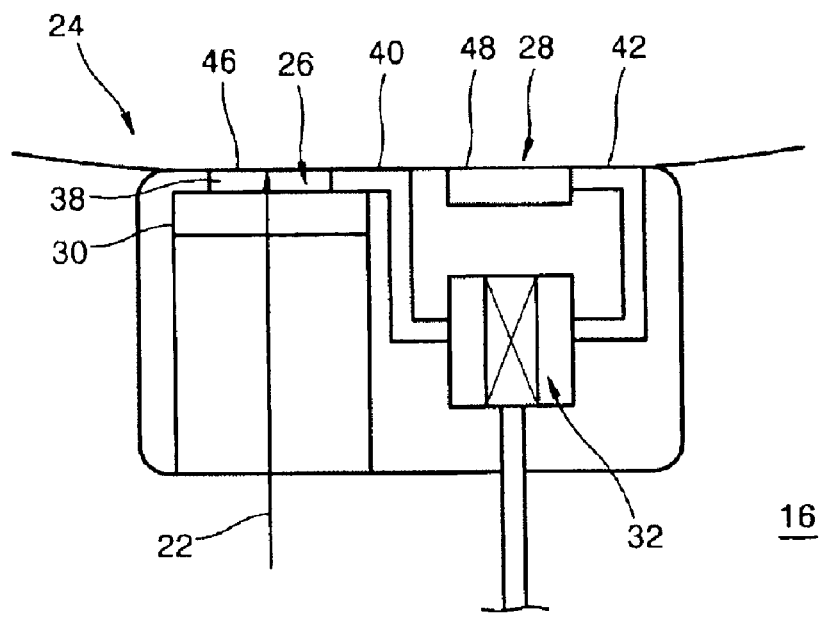
FIG. 2 illustrates a probe of a conventional device for non-invasively measuring blood glucose using photoacoustic spectroscopy, as shown in FIG. 1.

Korean Patent Application No. 2002-15147, filed Mar. 20, 2002, and entitled: "Apparatus and Method for Non-Invasively Measuring Bio-Fluid Concentrations by Using Photoacoustic Spectroscopy," is incorporated by reference herein in its entirety.

Hereinafter, an apparatus and a method for non-invasively measuring bio-fluid concentrations and a method thereof will be described in greater detail with reference to the accompanying drawings. Like reference numerals refer to like elements throughout.

Figure 3:
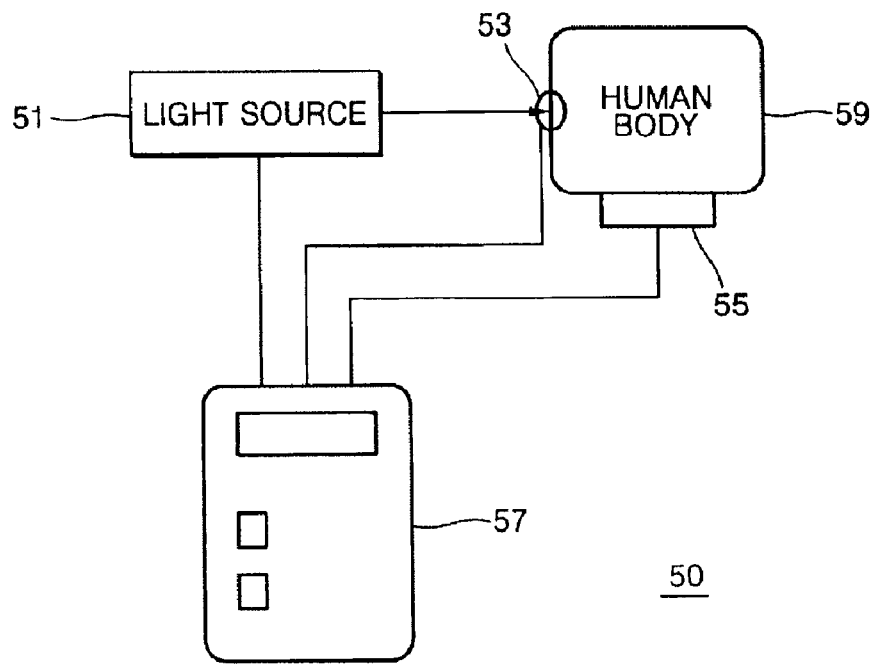
FIG. 3 is a block diagram of a device for non-invasively measuring bio-fluid concentrations according to an embodiment of the present invention.

FIG. 3 is a block diagram of an apparatus for non-invasively measuring bio-fluid concentrations according to an embodiment of the present invention. Referring to FIG. 3, an apparatus 50 for non-invasively measuring bio-fluid concentrations includes a light source 51, an acoustic signal generator 53 located close to an object of measurement, e.g., a human body 59, to which an incident light is applied, an ultrasonic translator 55 located close to another side of the object of measurement 59, a light detector (not shown) for detecting an intensity E of the incident light, a controller, a calculator, and an indicator 57. The controller, the calculator, and the indicator 57 are connected to the light source 51 and the ultrasonic translator 55.

In operation, the light source 51 applies an incident light having a predetermined frequency on a predetermined part of the human body 59. A targeted component of a living body absorbs the incident light. Here, the targeted component of the human body 59 may represent a bio-fluid, such as glucose, hemoglobin, albumin, cholesterol, or the like, which absorbs light beams of predetermined wavelengths depending on their characteristics. The predetermined part of the human body 59 may be a finger or the like.

When the incident light is absorbed by the predetermined part of the human body 59, waves of a predetermined wave length band are absorbed by the targeted component. The ultrasonic translator 53, then detects a photoacoustic PA signal generated and modulated by the absorption of the wavelengths. Next, the acoustic signal generator 53 generates a first acoustic signal A1 having a frequency similar to that of the photoacoustic PA signal in the vicinity of the human body 59.

The ultrasonic translator 55 detects the photoacoustic signal PA which has passed through the predetermined part of the human body 59. As described above, the ultrasonic translator 55 detects a second acoustic signal A2 that is generated when the first acoustic signal A1 generated from the acoustic signal generator 53 passes through the predetermined part of the human body 59 and thus is modulated due to the acoustic characteristics of the human body 59.

If electrons in a targeted component, such as a bio-fluid, absorb light beams, they move to a higher energy level. Subsequently, the electrons return to a lower energy level, thus generating sound waves.

The light detector measures the intensity E of light beams, i.e., an incident light generated from the light source 51.

The controller controls the light source 51 and the acoustic signal generator 53 so that the first acoustic signal A1 of a predetermined frequency band can be generated. The calculator calculates a signal compensation value N based on the intensity E of an incident light input from the light source 51, the photoacoustic signal PA input from the ultrasonic translator 55 and a coefficient of sound wave transmission $A_C$. Next, the calculator calculates a concentration C of the targeted component. Here, the signal compensation value N is preferably proportional to the concentration C of the targeted component.

The apparatus 50 for measuring bio-fluid concentrations may further include an indicator 57 that indicates the concentration C of the targeted component. As shown in FIG. 3, the light detector, the controller, the calculator, and the indicator 57 may be integrated into one unit in the apparatus 50 for measuring bio-fluid concentrations. Alternatively, only some of the light detector, the controller, the calculator, and the indicator 57 may be integrated into one unit. For example, the controller and the calculator 57 may be integrated into one unit, and the acoustic signal generator 53 and the ultrasonic translator 55 may be integrated into another unit. Alternatively, the light source 51, the acoustic signal generator 53, and the ultrasonic translator 55 may be integrated into one unit.

Figure 4:
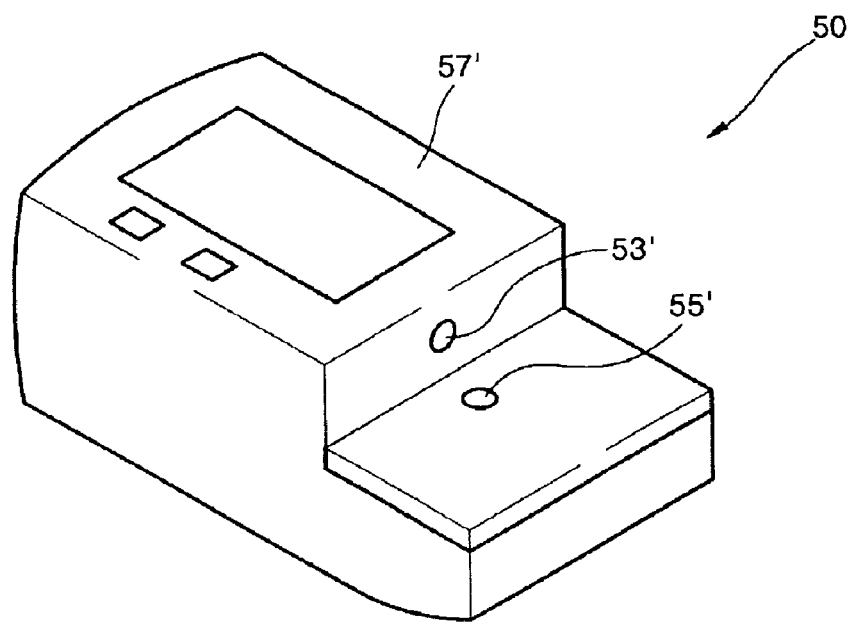
FIG. 4 illustrates a perspective view of a penetration-type device for non-invasively measuring bio-fluid concentrations according to an embodiment of the present invention.

FIG. 4 is a diagram of an example of the apparatus 50 of measuring bio-fluid concentrations, in which the light source 51, the acoustic signal generator 53, the ultrasonic translator 55, the light detector, the controller, the calculator, and the indicator 57 are integrated into one unit. Reference numeral 53' indicates an exit, through which an incident light generated from the light source 51 and the first acoustic signal A1 generated from the acoustic signal generator 53 are emitted. Reference numeral 55' indicates an entrance through which the photoacoustic signal PA and the second acoustic signal A2 pass to enter the ultrasonic translator 55. Reference numeral 57' indicates a predetermined unit, into which a light detector, a controller, a calculator, and an indicator are integrated.

Figure 5:
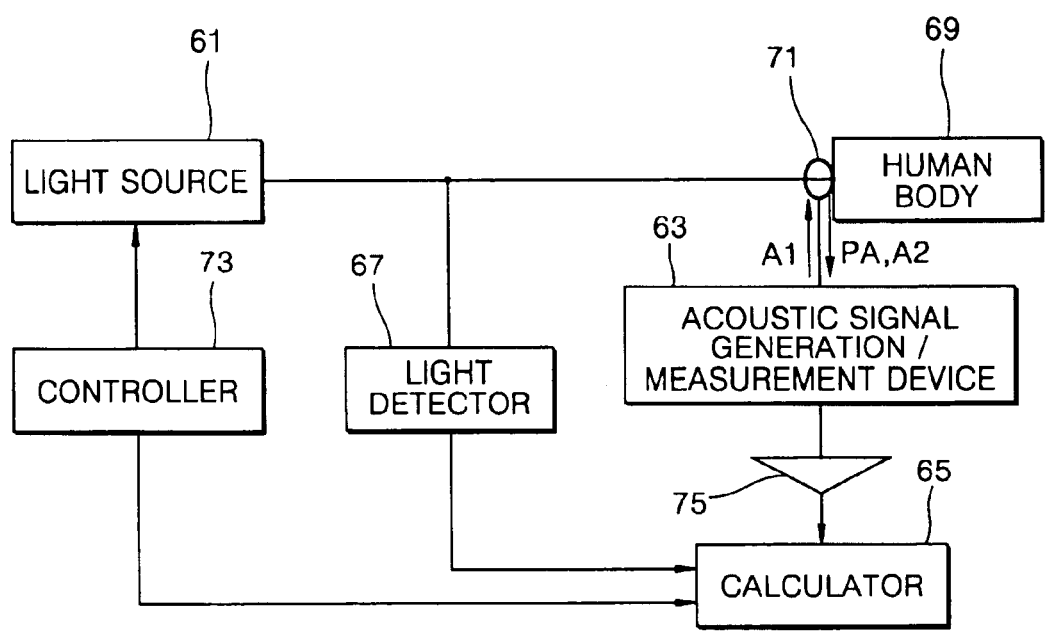
FIG. 5 is a block diagram of a reflection-type device for non-invasively measuring bio-fluid concentrations according to an embodiment of the present invention.

FIG. 5 is a block diagram of an apparatus for measuring bio-fluid concentrations according to another embodiment of the present invention. Referring to FIG. 5, an apparatus for measuring bio-fluid concentrations includes a light source 61, which applies an incident light of a predetermined frequency band that can be absorbed into a part of a human body 69, and an acoustic signal generation/measurement device 63, which generates to an ultrasonic translator 71 a first acoustic signal A1 having a similar frequency band to that of a photoacoustic signal PA in the vicinity of the part of the human body 69. The acoustic signal generation/measurement device 63 may include the ultrasonic translator 71. Here, the photoacoustic signal PA is generated when the incident light is reflected by the part of the human body 69 and waves of predetermined lengths are absorbed into a targeted component of the human body 69.

In addition, the apparatus for measuring bio-fluid concentrations further includes a light detector 67, which detects an intensity E of the incident light, a controller 73, which controls the acoustic signal generation/measurement device 63 so that a first acoustic signal A1 in a predetermined frequency band can be generated, a pre amplifier 75, which amplifies the photoacoustic signal PA and the second acoustic signal A2, and a calculator 65, which calculates a signal compensation value N based on the photoacoustic signal PA input from the ultrasonic translator 71, and the coefficient of sound wave transmission through the acoustic signal generation/measurement device 63, and then computes a concentration C of the targeted component based on the signal compensation value N.

The apparatus for measuring bio-fluid concentrations may further include an indicator (not shown), which indicates the concentration C of the targeted component. By way of further alternative, all or some of the light source 61, the controller 73, the calculator 65, the light detector 67, the ultrasonic translator 71, the acoustic signal generation/measurement device 63, and the indicator may be integrated into one unit.

Pulse-type heat expansion caused by light pulses generates acoustic pressure waves. The pressure waves p may be expressed by the following wave equation, equation 2:

$$\left[\frac{1}{v^2}\frac{\partial^2}{\partial t^2} - \nabla^2\right]p = \frac{\alpha\beta}{C_P}\frac{\partial I}{\partial t}. \tag{2}$$

In equation 2, I, $\alpha$, $\beta$, and v represent the intensity of light, the coefficient of optical absorption, the coefficient of heat expansion, and the velocity of sound waves, respectively. In addition, $C_P$ and t represent specific heat and time, respectively. The amplitude P of a Lai and Young pulse-shape photoacoustic signal may be expressed by the following equation, equation 3:

$$P \propto \alpha\beta\frac{\sqrt{v}}{C_P}E. \tag{3}$$

In equation 3, E refers to the intensity of light beams incident on the predetermined part of the human body 69.

As shown in equation 3, the photoacoustic signal may be derived in consideration of the optical characteristics of a medium, such as the intensity of incident beams or the coefficient of light absorption, the thermal characteristics of the medium, such as the coefficient of heat expansion, and the acoustic characteristics of the medium, such as the velocity of sound waves and the function of sound wave transmission. The thermal characteristics of the human body vary less considerably than the optical factors and the acoustic characteristics. Accordingly, it is possible to measure more precisely the absorption coefficient of the medium being tested by compensating for the optical and acoustic characteristics of the human body.

In the apparatus for measuring bio-fluid concentrations and the method thereof according to an embodiment of the present invention, the signal compensation value N is derived using equation 1 in order to compensate for the acoustic characteristics of the medium to be tested.

The signal compensation value N is proportional to the concentration C of the targeted component, as shown in the following equations, equations 4 and 5. The signal compensation value N may be compensated for by measuring sound waves and deriving the velocity v of the sound waves and the coefficient $A_C$, i.e., $$\frac{A2}{A1},$$

of sound wave transmission.

$$N = \frac{\alpha\beta\dfrac{\sqrt{v}}{C_P}A_C}{E\sqrt{v}\,A_C} \tag{4}$$

$$\alpha = k_h N \tag{5}$$

Here, $k_h$ is equal to $$\frac{C_P}{\beta}.$$

Since the coefficient of absorption may be derived from equation 5, the concentration C of the target component can be calculated by comparing the coefficient of absorption of a detected signal wave with the coefficient of absorption of a reference wave in order to measure bio-fluid concentrations.

In order to calculate the signal compensation value N, frequency analysis based on a Fourier transformation, or a wavelet analysis may be performed. Alternatively, the spatial characteristics of the human body may be compensated for by using a plurality of detectors.

Since the state of tissues may vary depending on the person, the part of the human body, and the time when the tissues are tested, such variation must be compensated for. In particular, in order to eliminate the influence of other components in the human body, the concentrations of other components may be searched in advance and may be compensated for, so that the concentration of the target component, such as glucose, may be more precisely calculated. For example, the concentration of water or hemoglobin may be determined using an optical method or by adding acoustic waves which are irradiated on tissues.

Figure 6:
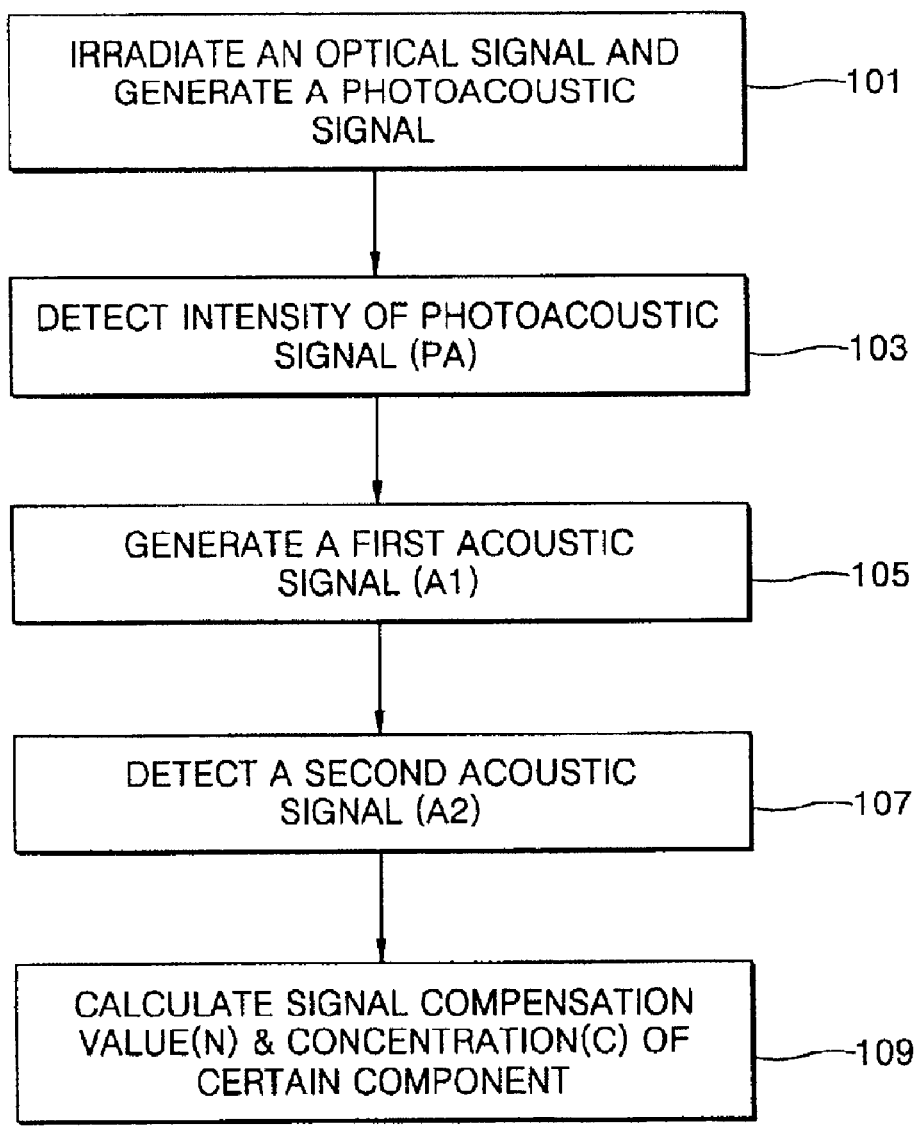
FIG. 6 is a flowchart of a method of non-invasively measuring bio-fluid concentrations according to an embodiment of the present invention.

FIG. 6 is a flowchart of a method for non-invasively measuring bio-fluid concentrations using photoacoustic spectroscopy according to an embodiment of the present invention. Referring to FIG. 6, in step 101, an incident light in a predetermined wavelength band, which is emitted from a light source, is irradiated on a predetermined part of a human body to be tested. When the incident light passes through or is reflected by the predetermined part, predetermined wavelengths are absorbed into a targeted component of the human body, and thus a photoacoustic signal PA is generated. Then, in step 103, the intensity P of the photoacoustic signal PA is detected. In step 105, a first acoustic signal A1 having a similar frequency band to that of the detected photoacoustic signal PA is generated.

When the first acoustic signal A1 passes through or is reflected by the component of the human body, predetermined wavelengths are absorbed into the component of the human body, and thus, in step 107, the attenuated second acoustic signal A2 is detected. Next, in step 109, a signal compensation value N or the concentration C of the targeted component of the human body is calculated based on the intensity E of the incident light, the detected photoacoustic signal PA, and the coefficient of sound wave transmission.

The concentration C of the targeted component may be derived based on the signal compensation value N, using equations 1, 4, and 5. As described above, the photoacoustic signal PA needs to be compensated for depending on the state of the human body, and this compensation can be performed using the signal compensation value N derived from equation 1.

FIGS. 7A through 7D are graphs showing the absorption spectra of glucose solutions in a near infrared ray range.

Figure 7A:
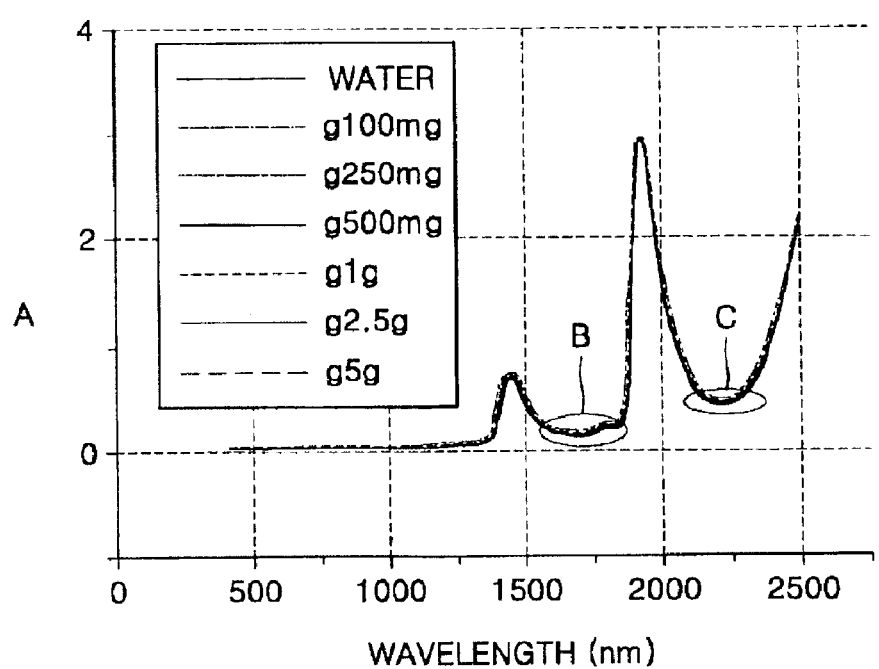
FIG. 7A is a graph showing the absorption spectra of glucose solutions in a range of near infrared light.

FIG. 7A shows the absorption spectra of glucose solutions having different amounts of glucose, i.e., 100 mg, 250 mg, 500 mg, 1 g, 2.5 g, and 5 g, when applying a photoacoustic signal having a wavelength band ranging from 400 nm to 2500 nm to the glucose solutions. As shown in FIG. 7A, the seven glucose solutions show almost the same absorption spectrum, which means that the absorption of a photoacoustic signal varies depending on the amount of water in a glucose solution having a small amount of glucose.

Figure 7B:
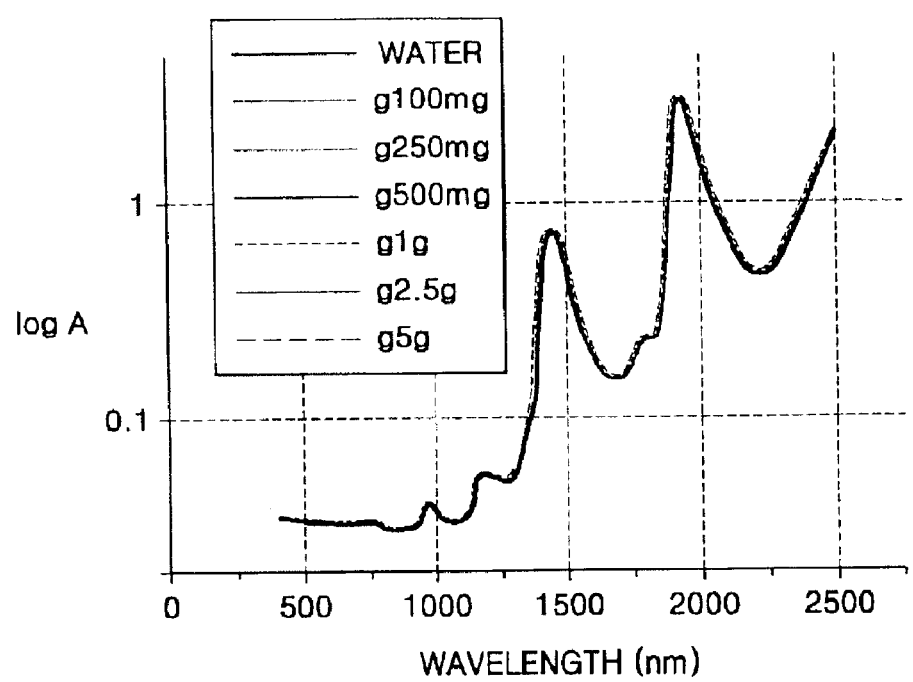
FIG. 7B is a graph showing the absorption spectra of glucose solutions of FIG. 7A on a logarithmic scale.

FIG. 7B is a graph showing the absorption spectra of glucose solutions of FIG. 7A on a logarithmic scale. In FIG. 7B, unlike in FIG. 7A, several small peaks appear near a wavelength of 1000 nm.

Figure 7C:
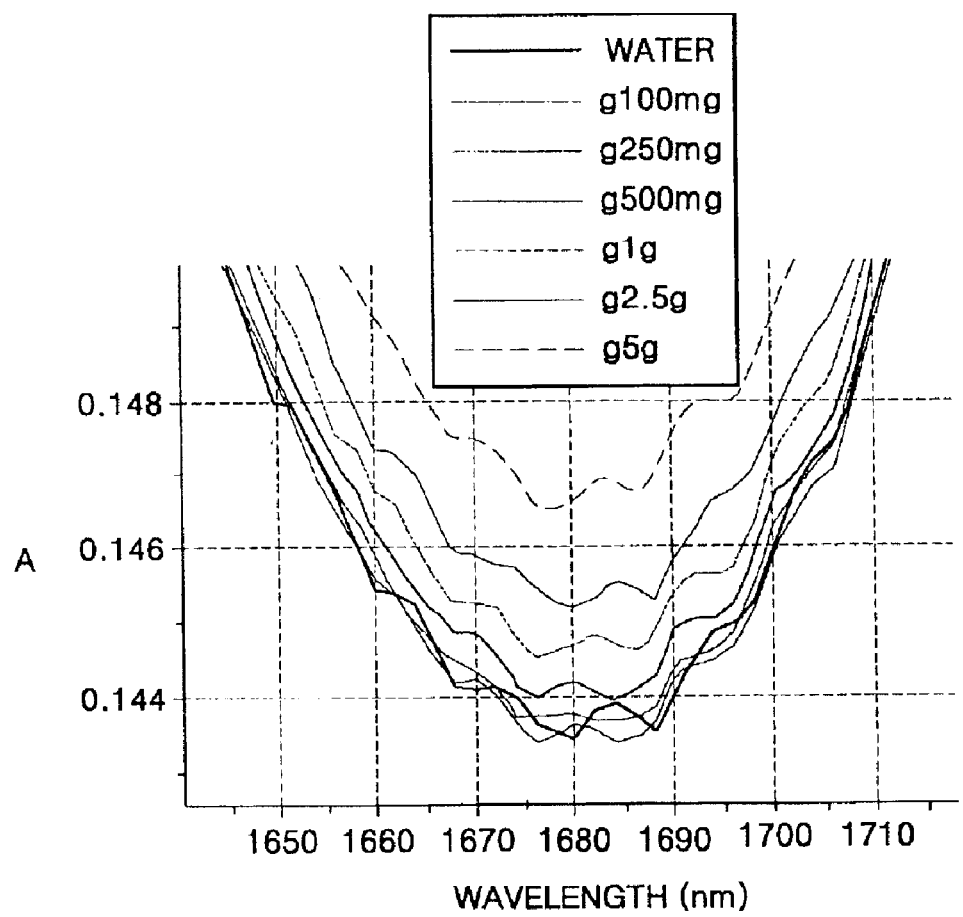
FIG. 7C is an enlarged view of region B of FIG. 7A.

FIG. 7C is an enlarged view of region B of FIG. 7A. As shown in FIG. 7C, a glucose solution having 100 mg of glucose shows a similar absorption spectrum to that of water. On the other hand, as the amount of glucose in a glucose solution increases to 5 g, the distance between the absorption spectrum of the glucose solution and the absorption spectrum of water increases. FIG. 7C shows that the absorption spectrum of a glucose solution varies depending on the concentration when applying a photoacoustic signal having a wavelength band of 1660 nm–1700 nm to the glucose solution.

Figure 7D:
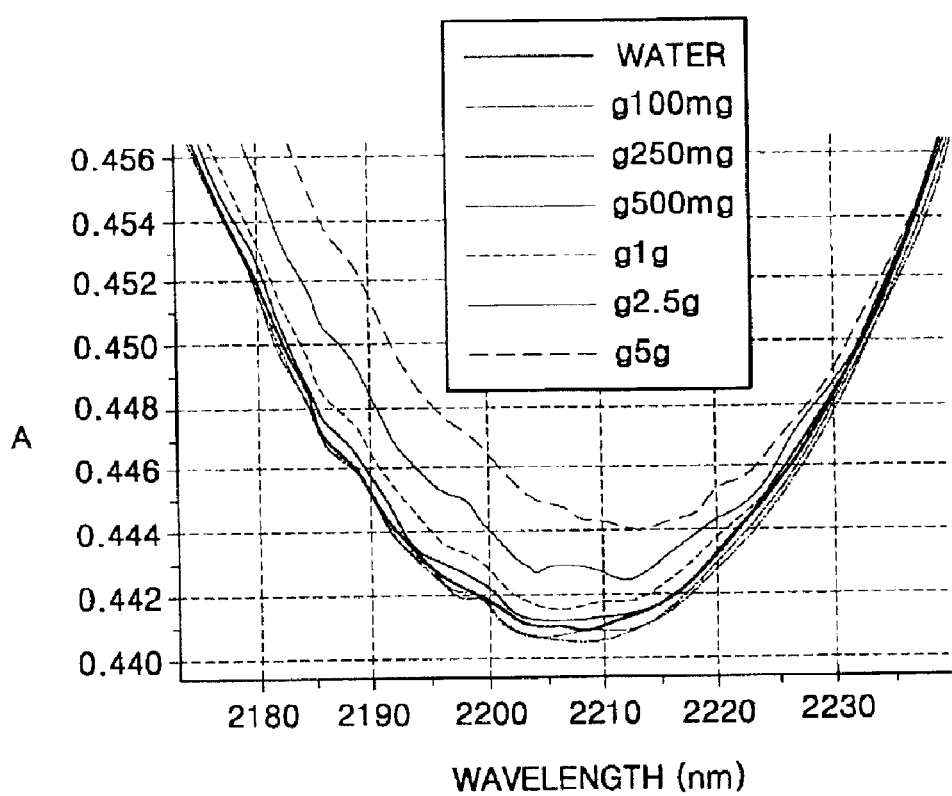
FIG. 7D is an enlarged view of region C of FIG. 7A.

FIG. 7D is an enlarged view of region C of FIG. 7A. In FIG. 7D, the phenomenon that the more glucose in a glucose solution, the higher absorption rate of a photoacoustic signal is distinctively shown near a wavelength range of about 2190 nm–2220 nm.

According to the results of the aforementioned experiments, it is possible to conclude that photoacoustic signals having a wavelength band of about 1600 nm–1800 nm, a wavelength band of about 2100–2280 nm, or a wavelength band of about 9–10 μm can be used in a near infrared ray range to measure the concentration of glucose using the apparatus for measuring bio-fluid concentrations according to an embodiment of the present invention.

Figure 8:
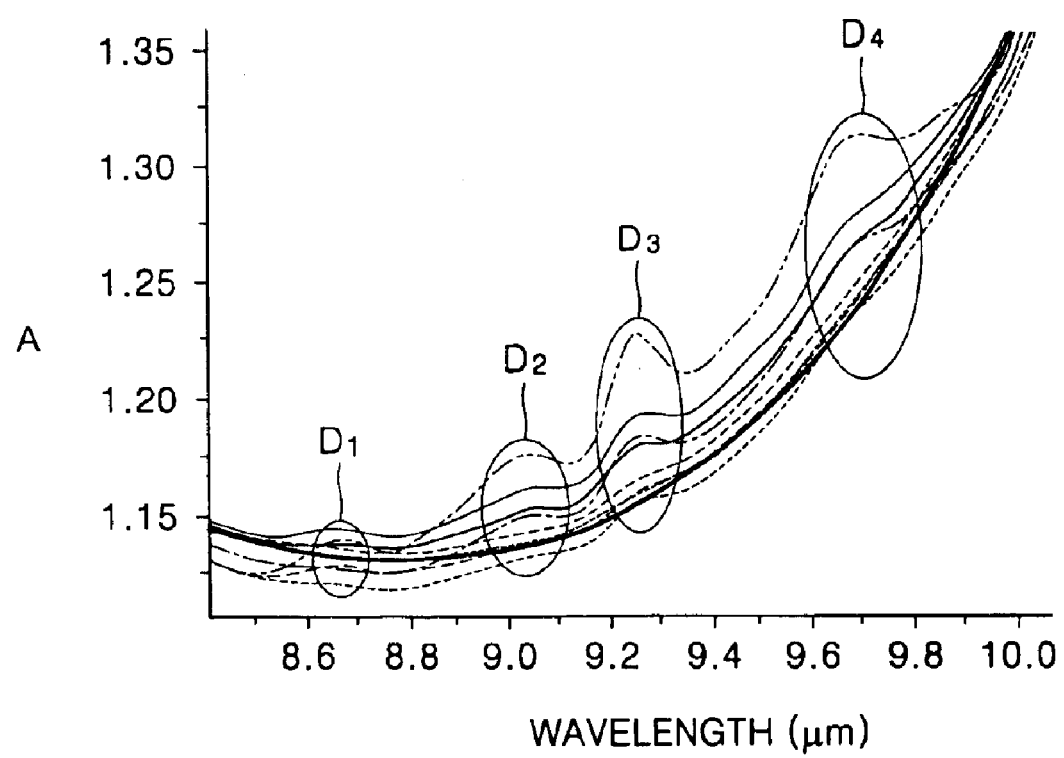
FIG. 8 is a graph showing the absorption spectra of glucose solutions in a range of far infrared light.

FIG. 8 is a graph showing the absorption spectra of glucose solutions in a far infrared light range. In FIG. 8, $D_1$, $D_2$, $D_3$, and $D_4$, at which peaks of the absorption spectra appear, represent important wavelengths bands near 8.7 μm, 9.0 μm, 9.3 μm, and 9.8 μm, respectively. In other words, when using the apparatus for measuring bio-fluid concentrations according to an embodiment of the present invention, it is preferable to use a photoacoustic signal having a wavelength range represented by $D_1$, $D_2$, $D_3$, or $D_4$ in a far infrared light range.

The method and apparatus for non-invasively measuring bio-fluid concentrations using photoacoustic spectroscopy according to the embodiments of the present invention can make up for the different transmission characteristics of a photoacoustic signal, which vary depending on the person and the part of the human body, by compensating for the photoacoustic signal varying depending on the kind or state of a living body.

Preferred embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims. For example, it is obvious to one skilled in the art that the different transmission characteristics of a photoacoustic signal can be compensated for using other compensating values.

What is claimed is:

1. An apparatus for non-invasively measuring bio-fluid concentrations comprising:

a light source for irradiating an incident light having a predetermined wavelength band which can be absorbed into a targeted component of a living body on a predetermined part of a living body;

an acoustic signal generator for generating a first acoustic signal A1 having a similar frequency band to the frequency band of a photoacoustic signal PA that is generated when the incident light is absorbed into the targeted component of the living body in the vicinity of the predetermined part of the living body;

a ultrasonic translator for detecting the photoacoustic signal PA and a second acoustic signal A2 that is a modulated signal of the first acoustic signal A1 due to the acoustic characteristics of the living body;

a controller for generating the first acoustic signal A1 in a predetermined frequency band;

a light detector for detecting an intensity E of the incident light; and a calculator capable of calculating a signal compensation value N based on the intensity E of the incident light from the light source, the photoacoustic signal PA input from the ultrasonic translator, and a coefficient of sound wave transmission $A_C$, and capable of computing a concentration C of the targeted component.

2. The apparatus as claimed in claim 1, further comprising an indicator for indicating the concentration C of the targeted component.

3. The apparatus as claimed in claim 2, wherein the concentration C of the targeted component is proportional to the signal compensation value N.

4. The apparatus as claimed in claim 2, wherein the light detector, the controller, the calculator, and the indicator are integrated into one unit.

5. The apparatus as claimed in claim 4, wherein the acoustic signal generator and the ultrasonic translator are integrated into one unit.

6. The apparatus as claimed in claim 4, wherein the light source, the acoustic signal generator, and the ultrasonic translator are integrated into one unit.

7. The apparatus as claimed in claim 1, wherein the light detector, the controller, and the calculator are integrated into one unit.

8. The apparatus as claimed in claim 7, wherein the acoustic signal generator and the ultrasonic translator are integrated into one unit.

9. The apparatus as claimed in claim 7, wherein the light source, the acoustic signal generator, and the ultrasonic translator are integrated into one unit.

10. The apparatus as claimed in claim 1, wherein the acoustic signal generator and the ultrasonic translator are integrated into one unit.

11. The apparatus as claimed in claim 1, wherein the light source, the acoustic signal generator, and the ultrasonic translator are integrated into one unit.

12. The apparatus as claimed in claim 1, wherein the acoustic signal generator is able to be fixed to a human body using an air pumping method.

13. The apparatus as claimed in claim 1, wherein the light source is any one of a laser diode (LD), a light emitting diode (LED), a laser, a black body radiator, or a lamp.

14. The apparatus as claimed in claim 1, wherein the photoacoustic signal has a wavelength band of about 1600 nm–1800 nm.

15. The apparatus as claimed in claim 1, wherein the photoacoustic signal has a wavelength band of about 2100–2280 nm.

16. The apparatus as claimed in claim 1, wherein the photoacoustic signal has a wavelength band of about 9–10 μm.

17. An apparatus for non-invasively measuring bio-fluid concentrations comprising:
   a light source for irradiating an incident light having a predetermined wavelength band which can be absorbed into a targeted component of a living body on a predetermined part of a living body;
   a light detector for detecting an intensity E of the incident light;
   an acoustic signal generation/measurement device for detecting a photoacoustic signal generated when the incident light is absorbed into the targeted component of the living body, for generating a first acoustic signal A1 having a similar frequency band to the frequency band of the photoacoustic signal PA in the vicinity of the predetermined part of the living body and for measuring a second acoustic signal A2 that is a modulated signal of the first acoustic signal A1 due to the acoustic characteristics of the living body;
   a controller for controlling the acoustic signal generation/measurement device so that the first acoustic signal A1 in a predetermined frequency band can be generated; and
   a calculator capable of calculating a signal compensation value N based on the intensity E of the incident light from the light source, and the photoacoustic signal PA from the acoustic signal generation/measurement device and a coefficient of sound wave transmission $A_C$, and capable of computing the concentration C of the targeted component.

18. The apparatus as claimed in claim 17, further comprising an indicator for indicating the concentration C of the targeted component.

19. The apparatus as claimed in claim 18, wherein the controller, the calculator, and the indicator are integrated into one unit.

20. The apparatus as claimed in claim 19, wherein the acoustic signal generation/measurement device and the light detector are integrated into one unit.

21. The apparatus as claimed in claim 19, wherein the light source, the acoustic signal generation/measurement device and the light detector are integrated into one unit.

22. The apparatus as claimed in claim 17, wherein the concentration C of the targeted component is proportional to the signal compensation value N.

23. The apparatus as claimed in claim 17, wherein the controller and the calculator are integrated into one unit.

24. The apparatus as claimed in claim 23, wherein the acoustic signal generation/measurement device and the light detector are integrated into one unit.

25. The apparatus as claimed in claim 23, wherein the light source, the acoustic signal generation/measurement device and the light detector are integrated into one unit.

26. The apparatus as claimed in claim 17, wherein the acoustic signal generation/measurement device and the light detector are integrated into one unit.

27. The apparatus as claimed in claim 17, wherein the light source, the acoustic signal generation/measurement device and the light detector are integrated into one unit.

28. The apparatus as claimed in claim 17, wherein the acoustic signal generator is able to be fixed to a human body using an air pumping method.

29. The apparatus as claimed in claim 17, wherein the light source is any one of a laser diode (LD), a light emitting diode (LED), a laser, a black body radiator, or a lamp.

30. The apparatus as claimed in claim 17, wherein the photoacoustic signal has a wavelength band of about 1600 nm–1800 nm.

31. The apparatus as claimed in claim 17, wherein the photoacoustic signal has a wavelength band of about 2100–2280 nm.

32. The apparatus as claimed in claim 17, wherein the photoacoustic signal has a wavelength band of about 9–10 μm.

33. A method for non-invasively measuring bio-fluid concentrations comprising:
   applying an incident light having a predetermined wavelength band which can be absorbed into a targeted component of a living body to a predetermined part of the living body;
   detecting the intensity E of the incident light and a photoacoustic signal PA generated when predetermined wavelengths of the incident light are absorbed into the targeted component of the living body;
   generating a first acoustic signal A1 having a similar frequency band to the frequency band of the photoacoustic signal PA in the vicinity of the predetermined part of the living body;
   detecting a second acoustic signal A2 that is a modulated signal of the first acoustic signal A1 due to the acoustic characteristics of the living body; and
   calculating a signal compensation value N based on the intensity of the incident light, the photoacoustic signal PA and a coefficient of sound wave transmission $A_C$, and computing a concentration C of the targeted component of the living body.

34. The method as claimed in claim 33, wherein the concentration C of the targeted component of the living body is proportional to the signal compensation value N.

35. The apparatus as claimed in claim 33, wherein the photoacoustic signal has a wavelength band of about 1600 nm–1800 nm.

36. The apparatus as claimed in claim 33, wherein the photoacoustic signal has a wavelength band of about 2100–2280 nm.

37. The apparatus as claimed in claim 33, wherein the photoacoustic signal has a wavelength band of about 9–10 μm.

* * * * *